United States Patent
Wijbrans et al.

(10) Patent No.: US 9,854,961 B2
(45) Date of Patent: Jan. 2, 2018

(54) PHOTONIC NEEDLE WITH OPTIMAL BEVEL ANGLE

(71) Applicant: KONINKLIJKE PHILIPS N.V., Eindhoven (NL)

(72) Inventors: Klaas Cornelis Jan Wijbrans, Rijen (NL); Gerhardus Wilhelmus Lucassen, Eindhoven (NL); Bernardus Hendrikus Wilhelmus Hendriks, Eindhoven (NL); Christian Reich, Eindhoven (NL); Johannes Antonius Van Rooij, Best (NL); Waltherus Cornelis Jozef Bierhoff, Veldhoven (NL); Marjolein Van Der Voort, Valkenswaard (NL); Axel Winkel, Zapel-Hof (DE); Stephan Voss, Schwerin (DE); Torre Michelle Bydlon, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 82 days.

(21) Appl. No.: 14/776,761

(22) PCT Filed: Apr. 3, 2014

(86) PCT No.: PCT/IB2014/060400
§ 371 (c)(1),
(2) Date: Sep. 15, 2015

(87) PCT Pub. No.: WO2014/162289
PCT Pub. Date: Oct. 9, 2014

(65) Prior Publication Data
US 2016/0007841 A1    Jan. 14, 2016

Related U.S. Application Data

(60) Provisional application No. 61/807,839, filed on Apr. 3, 2013, provisional application No. 61/836,780, filed on Jun. 19, 2013.

(30) Foreign Application Priority Data

Feb. 14, 2014  (EP) .................................. 14155142
Feb. 14, 2014  (EP) .................................. 14155150

(51) Int. Cl.
*A61B 6/00* (2006.01)
*A61B 1/07* (2006.01)
*A61B 5/00* (2006.01)

(52) U.S. Cl.
CPC .............. *A61B 1/07* (2013.01); *A61B 5/0084* (2013.01); *A61B 5/6848* (2013.01)

(58) Field of Classification Search
CPC ........ A61B 1/07; A61B 5/0084; A61B 5/6848
See application file for complete search history.

(56) References Cited

U.S. PATENT DOCUMENTS 5,257,991 A   11/1993  Fletcher et al.
5,280,788 A    1/1994  Janes
(Continued)

OTHER PUBLICATIONS

Desjardins, A.E. et al. "Epidural needle with embedded optical fibers for spectroscopic differentiation of tissue: ex vivo feasibility study", Biomed Opt Express. Jun. 1, 2011 2(6): 1452-1461.
(Continued)

*Primary Examiner* — Robert N Wieland

(57) ABSTRACT

The present invention relates to a medical needle which comprises an elongate tube and at least one optical fiber, e.g. two fibers, arranged within the elongate tube, for making optical measurements at the distal end of the needle. The optical fibers(s) has a beveled distal end surface, wherein a plane touching the beveled distal end surface and a longitudinal extension axis of the optical fiber forms a bevel angle which is 30°-35°. Such needle is advantageous for providing a medical needle which is reliable and long term stable, can be manufactured in low cost using known optical fiber
(Continued)

materials, thus allowing it to form part of disposable medical kits. Still, the bevel angle of 30°-35° provides a needle which is easy to insert and which provides a low tendency to cause tissue sticking. Especially, the elongate tube and the optical fiber end(s) have the same beveled angle within the range 30°-35°, thus allowing a smooth front surface of the needle.

16 Claims, 4 Drawing Sheets

(56) References Cited

U.S. PATENT DOCUMENTS

| | | |
|---|---|---|
| 8,812,080 B2 | 8/2014 | Nachabe |
| 2008/0306391 A1 | 12/2008 | Hular et al. |
| 2011/0251494 A1 | 10/2011 | Hendriks et al. |
| 2012/0029360 A1 | 2/2012 | Hendriks |
| 2014/0121538 A1 | 5/2014 | Hendriks |
| 2014/0236024 A1 | 8/2014 | Bierhoff et al. |
| 2015/0057530 A1* | 2/2015 | Roggeveen .......... A61B 5/0053 600/424 |
| 2016/0007841 A1* | 1/2016 | Wijbrans ............. A61B 5/6848 600/182 |

OTHER PUBLICATIONS

Nachabe, R. et al. "Estimation of lipid and water concentrations in scattering media with diffuse optical spectroscopy from 900 to 1600 nm", Journal of Biomedical Optics 15(3), 1 (May/Jun. 2010), p. 1-1 to 1-11.

Farrell, T.J. et al. "A diffusion theory model of spatially resolved, steady-state diffuse reflectance for the noninvasive determination of tissue optical properties in vivo", Med. Phys. 19(4), Jul./Aug. 1992, p. 879-888.

* cited by examiner

PHOTONIC NEEDLE WITH OPTIMAL BEVEL ANGLE

CROSS-REFERENCE TO PRIOR APPLICATIONS

This application is the U.S. National Phase application under 35 U.S.C. §371 of International Application Ser. No. PCT/IB2014/060400, filed on Apr. 3, 2014, which claims the benefit of U.S. Applications Ser. Nos. 61/807,839 and 61/836,780, filed on Apr. 3, 2013 and Jun. 19, 2013 and EP Applications 14155142.4 and 14155150.7 both filed on Feb. 14, 2014. These applications are hereby incorporated by reference herein.

FIELD OF THE INVENTION

The invention relates to a photonic or optical needle, i.e. a needle which incorporates optical fiber(s) or waveguide(s). Especially, the invention provides a medical needle suitable for performing optical measurements at the tip of the medical needle in biological tissue.

BACKGROUND OF THE INVENTION

In the fields of anaesthesia and pain management the need to accurately position a medical needle within the body is frequently encountered. Such needles may be used in the delivery of fluid, such as an anaesthetic reagent, wherein the position of the delivery of the fluid is important in achieving an optimal effect or in avoiding potentially damaging side effects. Likewise, medical needles that are used to perform a biopsy should be accurately positioned in order to ensure that the correct tissue sample is taken from the body.

Medical photonic needles with optical fibers inside are known. Such needles allow optical probing of biological tissue, e.g. for positioning or for other purposes and typically have one light-supplying fiber and one light-receiving fiber. In alternative configurations a single fiber performs both light-supplying and light-receiving functions.

In the original concept of the photonic needle, a needle with straight ended fibers at the tip was used as disclosed in patent application WO2013054254A.

Medical photonic needles having optical fibers in which the end surface of the optical fibers are beveled, are also known. See for example "*Epidural needle with embedded optical fibers for spectroscopic differentiation of tissue: ex vivo feasibility study*" by Desjardins et al, Biomed Opt Express. 2011 Jun. 1; 2(6): 1452-1461. In this publication the beveled surface of the needle was angled at 20 degrees with respect to the needle axis. Three optical fibers were embedded in a cannula with epoxy and polished so that their distal ends were flush with the beveled surface. Such a small bevel angle provides a sharp point that facilitates insertion into a body.

Medical photonic needles in general however, suffer from a number of problems.

The optical performance of medical photonic needles having both straight-cut and beveled optical fiber(s) is conventionally calibrated in air by placing a reference optical surface in front of the light supplying fiber such that light is directed back into the light receiving fiber. The optical performance is determined on the basis of the proportion of supplied light that is subsequently received, and on the basis of the optical properties of the reference optical surface.

A problem resulting from the usual in-air calibration is that the amount of internal reflection of light within the optical fiber at the fiber tip is dependent upon the refractive index of the optical medium that is in contact with the fiber tip. Since this optical medium is air, having a refractive index of unity, during calibration, the differing refractive index of tissue during use of the medical needle, means that the in-air calibration data has limited relevance. In order to resolve this issue is it also known to calibrate the optical fibers of such medical needles in for example liquid media having a refractive index that is closer-matched to that of tissue.

The present invention seeks to improve the robustness of the optical calibration of such photonic needles.

SUMMARY OF THE INVENTION

The present invention relates to optical needles having one or more optical fibers and arises from the insight that the effects of internal reflection at the fiber tip are exacerbated at small bevel angles, thus in optical needles having a sharp tip. As the bevel angle of such an optical fiber is decreased and the fiber tip becomes sharper, the proportion of light emitted sideways in a side-lobe, termed an indirect beam, in relation to that emitted in a direct, or forward-looking beam, is increased. When an in-air calibration is performed with such a configuration, much of the light emitted by an optical fiber having a small bevel angle is emitted in the indirect beam and may miss the reference optical surface entirely. However when the same sharp bevel angle optical fiber is placed in tissue, the proportion of light in the indirect beam falls significantly owing to the closer match between the refractive index of the optical fiber and that of the tissue, thereby rendering the calibration of little relevance. This degrades the robustness of the calibration procedure and increases the amount of time needed for calibration due to the need to integrate low signal levels over time. The lack of robustness has multiple causes in addition to the mix of direct and internal reflected light distribution described above. These include the influence of the fiber buffer material and its thickness on the color of the reflected light, the insight that minute changes in bevel angle result in large changes in the ratio between internal reflected light and direct output light, the inconsistency of the optical performance of the optical needle due to manufacturing variations, aging of both the buffer material and the fixating glue under the buffer material, and the sensitivity to the angle under which calibration is performed in air.

In tissue, at a 20° bevel angle as used in a prior art photonic needle, a rather sharp needle, the light output from the optical fiber is a mix of indirect reflected light and direct light into the tissue because in tissue only part of the light will suffer from total internal reflection. The ratio between indirect light and direct light in tissue varies significantly with small changes of the bevel angle, meaning that even if a fixed ratio can be found because the buffer properties can be kept constant, still no robustness with the database can be achieved if individual needles have a slight variation of the bevel angle. As a result, it is no longer possible to calibrate in air. In addition, due to the light loss when reflecting on the buffer, a much longer calibration time will be required to perform the calibration without noise, which is not practical in the workflow. Finally, unlike the silica core of a fiber, the material for the buffer and the glue are organic polymers and thus suffer from changing optical characteristics due to aging. With a required five year shelf life, this is of importance for calibration.

Following the above, it is an object of the invention to provide a medical needle with improved positioning accuracy. It is further object to provide a medical needle having a needle tip with a reduced tendency to stick to the tissue or to trap tissue, and which is easy to insert in biological tissue. It is a further object to optimize light coupling for illumination and detection. It is a further object to provide a medical needle which should be possible to manufacture in a cost effective way, e.g. as disposable device. Still, it is a further object to provide a medical needle which has a reliable function even after a considerable time, e.g. after storage, in case the needle forms part of a disposable medical kit.

A first aspect of the invention provides a needle comprising:
an elongate tube having a beveled distal end, and
at least one optical fiber arranged within the elongate tube, wherein the optical fiber has a beveled distal end surface, wherein a plane touching the beveled distal end surface and a longitudinal extension axis of the optical fiber forms a bevel angle selected within a bevel angle range of 30°-35°.

Such optical needle is advantageous since, in essence, it has been found that the specified bevel angle within the range of 30°-35° of the optical fiber, and preferably the same angle for the elongate tube, allows a photonic needle which combines a number of benefits that are differently affected by the bevel angle. Such needle is suitable for medical applications, since it has a low degree of tissue sticking due to the rather sharp bevel angle, it is reliable due to a low sensitivity to material changes over time because optical side lobes can be eliminated which allows high calibration reliability. Finally, the needle can be manufactured using known low cost optical fiber types, thereby allowing the needle to be economically attractive to form part of disposable medical kits.

The invention is based on the insight of a relation between the bevel angle of the optical fiber, the refractive index of tissue and a light beam shape, especially the presence of optical side lobes, for specific and economically attractive materials. This insight combined with a number of other criteria, has resulted in providing a bevel angle of specifically 30°-35° as providing a needle with a number of combined properties which provides an especially attractive medical photonic needle.

A plane touching the beveled distal end of the elongate tube and a longitudinal extension axis of the elongate tube may form an angle within said bevel angle range (i.e. 30°-35°). A plane touching the beveled distal end of the elongate tube and a longitudinal extension axis of the elongate tube may form an angle which is equal to or substantially equal to said bevel angle. The plane touching the beveled distal end surface of the optical fiber and the plane touching the beveled distal end of the elongate tube may be substantially parallel. Especially, said two planes may be coinciding, i.e. the optical fiber end being arranged flush with the beveled distal end of the elongate tube. The needle may comprise a second optical fiber arranged within the elongate tube, wherein a plane touching the beveled distal end surface of the second optical fiber and a longitudinal extension axis of the second optical fiber forms a bevel angle (B A) selected within said bevel angle range (i.e. 30°-35°). Especially, the bevel angle of both a first and a second optical fibers are selected to be the same. Especially, the plane touching the beveled distal end surface of the first optical fiber, the plane touching the beveled distal end surface of second optical fiber, and the plane touching the beveled distal end of the elongate tube are all substantially parallel, such as all these three planes coinciding.

The bevel angle range may be one of: 30°-32°, 31°-33°, 32°-34°, and 33°-35°. Alternatively, the bevel angle range may be one of: 31°-32°, 32°-33°, 33°-34°, and 34°-35°. Alternatively, the bevel angle range may be one of: 30.5°-31.5, 31.5°-32.5°, 32.5°-33.5°, and 33.5°-35°. More alternatively, the bevel angle range may be one of: 30°-33°, 31°-34°, 32°-35°, 30°-34°, and 31°-35°. Still more alternatively, the bevel angle range may be one of: 30.5°-34.5, 31.0°-34.0°, 31.5°-33.5°, and 32.0°-33.0°.

In preferred embodiments, the optical fiber is made of a material comprising silica. Especially, the optical fiber can be made of undoped fused silica. Alternatively, the optical fiber can be made of F-doped fused silica, e.g. combined with a hard cladding. It has been found that an undoped fused silica fiber core can be used for the optical fiber and still provide the desired optical properties, thereby providing an attractive material for low cost manufacturing of a disposable medical needle kit.

A channel may be formed within the elongate tube, so as to allow transport of a fluid through the medical needle. Especially, the channel may have a wall which comprises at least a portion of the inner bore of the elongate tube, alternatively or additionally the channel may have a wall which further comprises at least a portion of the outer bore of a stylet insert, in case of embodiments in which a stylet insert within the elongate tube is used. As a still further option, the channel may be formed within a stylet insert.

The beveled distal end surface of the at least one optical fiber may be plane, e.g. such that a smooth plane surface which is polished.

The optical fiber end(s) may be coated with a coating covering the distal end surface of the at least one optical fiber. Such coating may comprise one of: Teflon®, Delrin®, silicon, and a lipophobic coating material. The thickness of a coating layer formed by such coating material may be such as 0.5-2 µm.

In preferred embodiments, the distal end surface of the at least one optical fiber has a slanting or bevel angle equal to or substantially equal to a slanting or bevel angle of the beveled distal end of the elongate tube. Especially, the slanting angle of the distal end surface of the at least one optical fiber is preferably equal to the slanting angle of the beveled distal end of the elongate tube, and arranged so as to form a plane coinciding with the plane touching the beveled distal end of the elongate tube. Hereby, an especially smooth surface of the medical needle can be provided, thus preventing sticking of tissue.

The at least one optical fiber may be arranged within a stylet insert, wherein the stylet insert has a bevel at the distal end that has substantially the same bevel angle as the beveled distal end of the elongate tube, and the stylet insert is arranged within the elongate tube such that a plane touching the beveled distal end of the elongate tube, and a plane touching the beveled distal end of the stylet insert are substantially parallel. Especially, such embodiment may comprise two or more optical fibers arranged within the stylet insert. E.g. one optical fiber for transmitting light, and one optical fiber for receiving reflected and/or light from the tissue.

It may be preferred that the elongate tube has a circular cross section.

In a second aspect, the invention provides an interventional device comprising a medical needle according to the first aspect.

In a further aspect, the invention provides a medical system comprising a needle according to the first aspect, and an optical console system comprising a light source and a light detector, and being arranged for optical connection to the at least one optical fiber, so as to allow optical interrogation of the at least one optical fiber.

In a still further aspect, the invention provides a method for optical probing in biological tissue, the method comprising:
  providing at least one optical fiber with a beveled distal end surface, wherein a plane touching the beveled distal end surface and a longitudinal extension axis of the at least one optical fiber forms a bevel angle selected within a bevel angle range of 30°-35°, and
  applying light to and/or receiving light from the biological tissue through the beveled end surface of the at least one optical fiber.

It is to be understood that the advantages and embodiments mentioned for the first aspect apply as well for the further aspects, and the mentioned embodiments of the first aspect may be combined in any way with the further aspects.

BRIEF DESCRIPTION OF THE FIGURES

It is to be understood that the illustrations are merely sketches, and thus the illustrations of the bevel angles should not be considered as exact illustrations.

DETAILED DESCRIPTION OF THE INVENTION

Figure 1A:
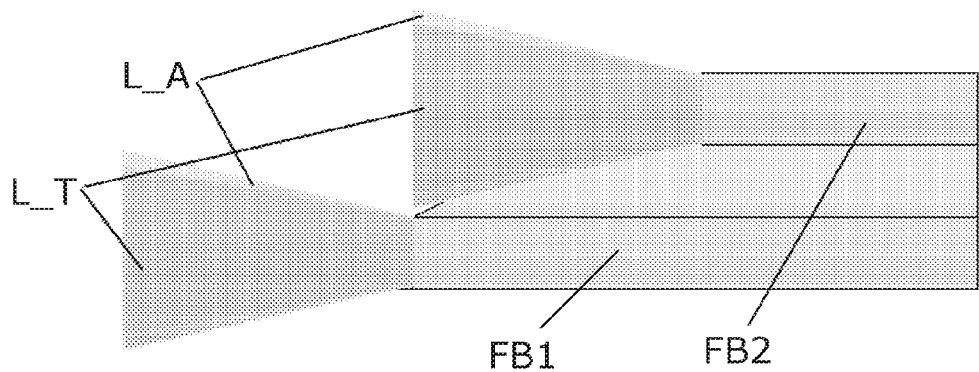
FIGS. 1a and 1b illustrate a prior art needle examples of light beams from optical fibers with a straight cut fiber end (FIG. 1a), and an optical fiber with a sharp cutting angle (FIG. 1b).

FIG. 1a shows a sketch of a prior art needle with two optical fibers FB1, FB2 with straight-cleaved fiber ends, and their respective light cones or beams in air L_A and in tissue L_T which is seen to be practically identical.

Figure 1B:
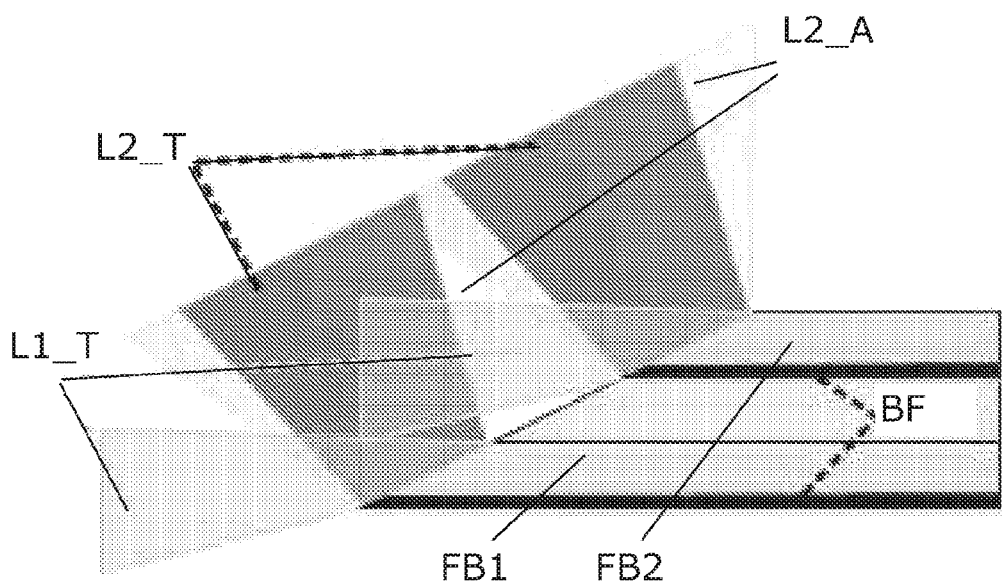

FIG. 1b shows a similar sketch of another prior art needle with beveled fiber ends with a bevel angle of 25°, i.e. a sharp needle. Here, resulting from internal reflection at the buffer BF, light beams from one fiber FB1, FB2 in tissue has two beams L1_T, L2_T, namely the desired forward beam L1_T and an undesired side lobe L2_T. The corresponding side lobe for air L2_A is also shown. As seen, a significant amount of the light in tissue L2_T is directed to the side of the needle.

Figure 2:
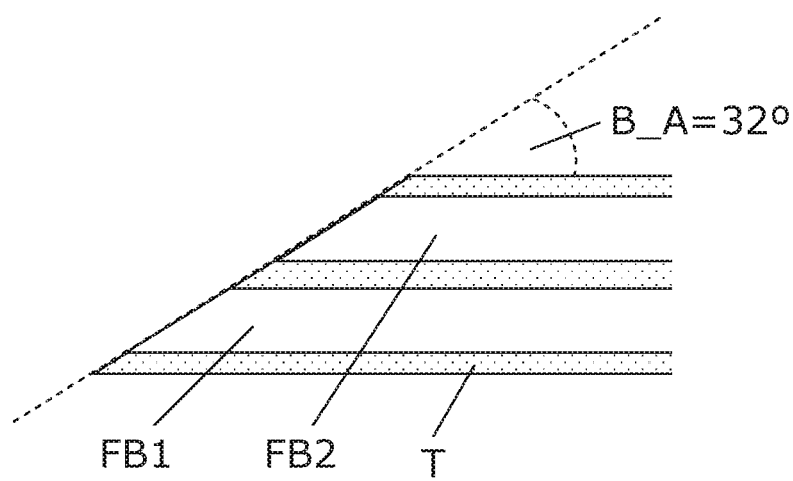
FIG. 2 illustrates a needle embodiment with two optical fibers cut in the same bevel angle as the elongate tube forming the needle structure, here illustrates with a bevel angle of 32°.

FIG. 2 shows a sketch of a needle embodiment with two optical fibers FB1, FB2 both with the same bevel angle B_A of 32° as the elongate tube T, e.g. metal tube, where the two fibers FB1, FB2 are arranged within a suitable cladding material. It is to be understood that a small deviation between bevel angle for the fiber ends FB1, FB2 and the elongate tube T end may be acceptable within normal production tolerances, such as e.g. +/−1°. However, in principle, to avoid tissue sticking, it is desirable to have a front surface of the needle which is as smooth as possible. To obtain this, the optical fibers FB1, FB2 are preferably cut with the same bevel angle as the elongate tube T.

Figure 3:
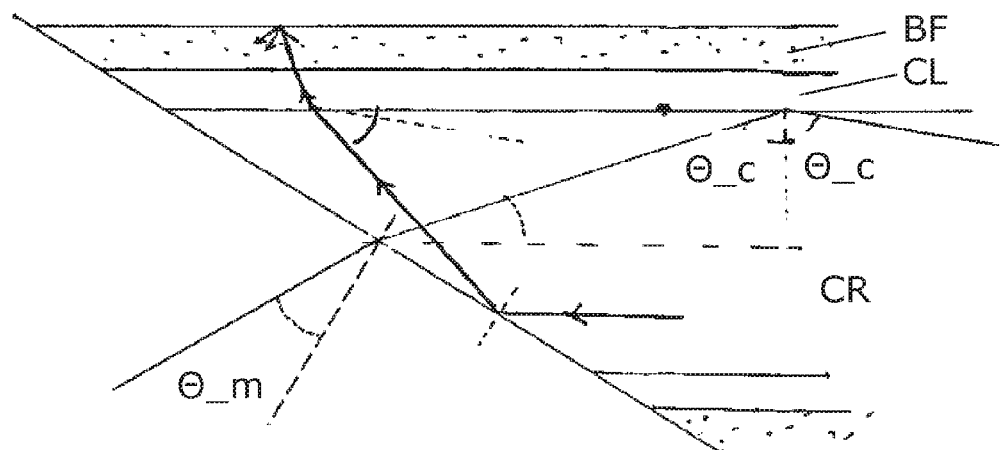
FIGS. 3 and 4 illustrate internal reflection in an optical fiber with slanting or beveled fiber end, and the use of reflecting coatings that around the optical fiber cladding at the distal end of the optical fibers in order to improve light delivery and collection.

FIG. 3 serves to illustrate light coupling for slanted or beveled optical fiber ends. Slanted fiber ends serve to prevent pockets that could cause tissue sticking. However, light output coupling with straight cut fibers is found to be more efficient compared to the light coupling with slanted fiber ends. Internal reflections at the slanted fiber interface cause light losses through the cladding CL and buffer BF. FIG. 3 illustrates step index fiber with core CR and cladding light is internally reflected for rays with an angle θ that is less than (90°-$θ_c$), where $θ_c$ is the critical angle at which the rays still undergo total internal reflection at the core cladding interface. Light coupling into or outwards from the fiber occurs for rays with angles θ less than $θ_m$. Internal reflection at a slanted fiber interface towards cladding CL and buffer BF causes reduced light output coupling for illumination and in coupling for detection since the angle θ, for these rays will be θ is greater than (90°-$θ_c$) and do not undergo total reflection but is transmitted to the buffer BF and can be absorbed and scattered by the buffer material.

Figure 4:
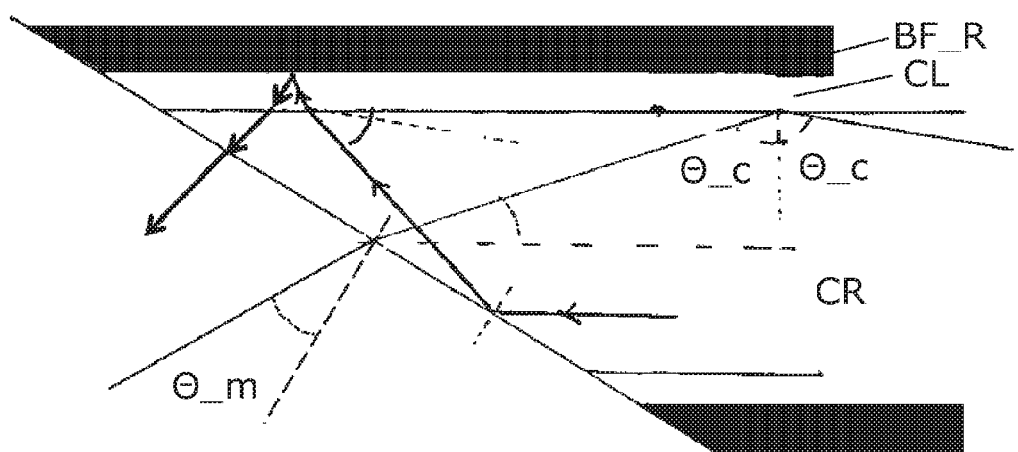

FIG. 4 illustrates the use of reflecting coatings BF_R that surround the optical fiber cladding CL at the distal end of the optical fibers in order to improve light delivery and collection. Such a reflective coating BF_R may be incorporated in a stylet which retains the optical fibers, or at the inside of the needle or cannula. Alternatively, a reflecting coating BF_R may be employed with polished pocket walls that are filled with index matching optically transparent material.

Figure 5:
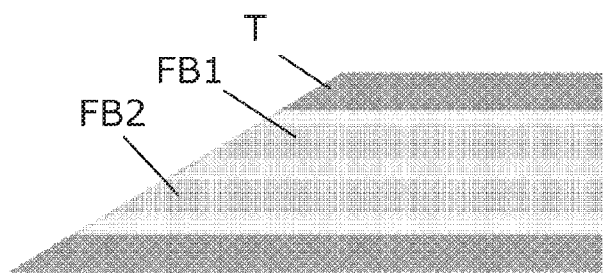
FIG. 5 illustrates a needle embodiment with a slanting or bevel angle of 31°.

FIG. 5 illustrates a needle embodiment with an elongate tube T and two optical fibers FB1, FB2 which all have one common bevel angle B_A of 31°, and wherein the optical fiber ends may be polished to form a specially smooth surface.

Figure 6:
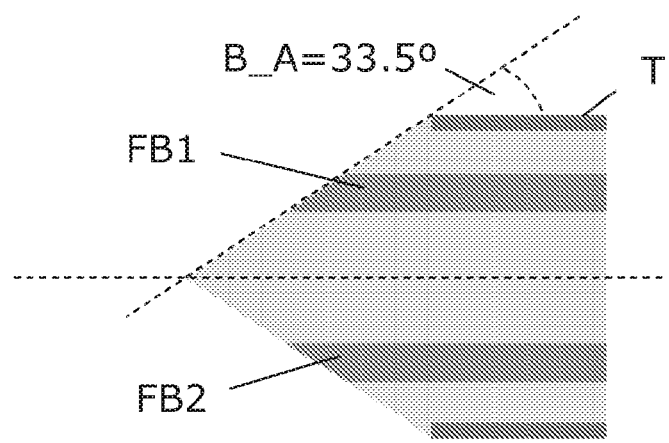
FIG. 6 illustrates a needle embodiment with a double beveled front.

FIG. 6 illustrates a needle with a double beveled distal and of B_A of 33.5°. As seen, one optical fiber FB 1 is positioned with its distal end flush with a first beveled part, whereas the second optical fiber FB2 is positioned with its distal end flush with a second beveled part. In the illustrated embodiment, the first and second beveled parts are symmetrical, i.e. both having the same bevel angle B_A, thereby forming a front of the needle with a 67° angle.

Figure 7:
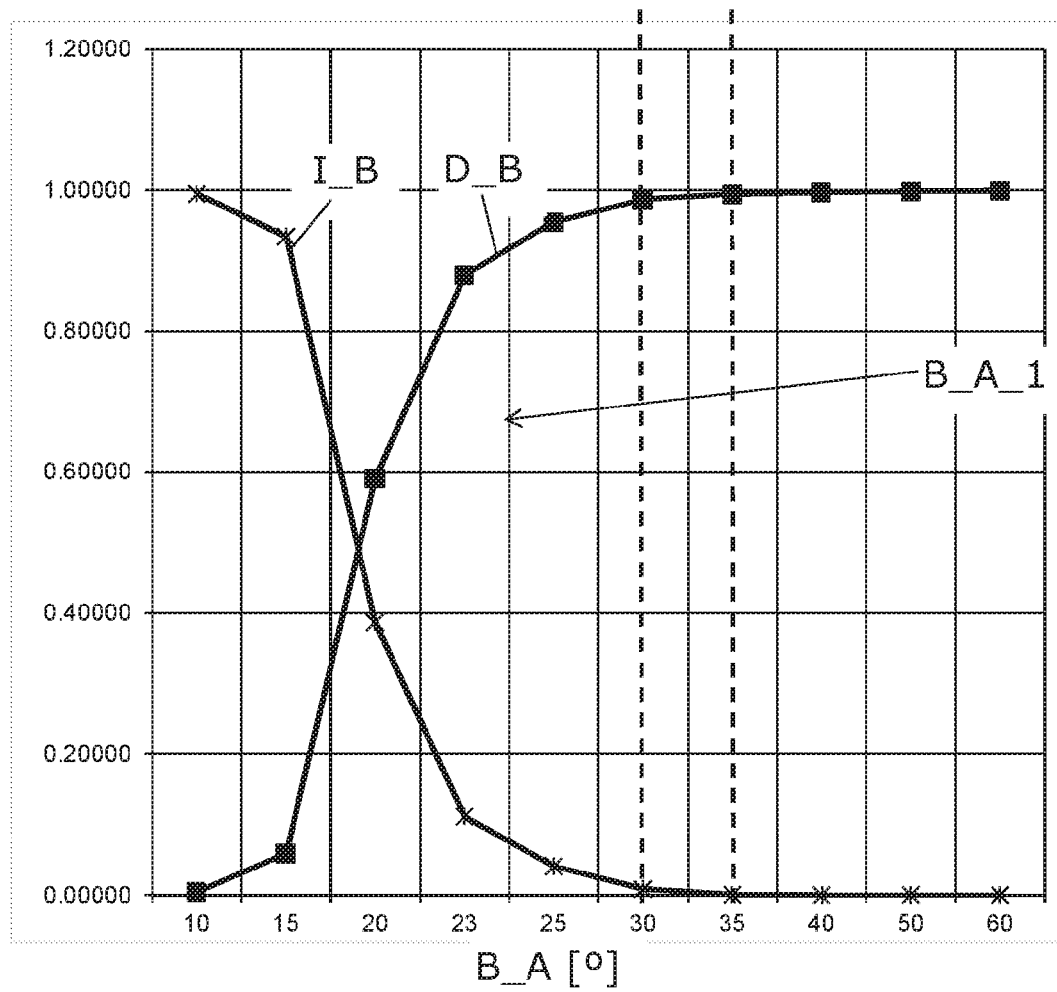
FIG. 7 illustrates a graph showing direct versus indirect beam from an optical fiber as a function of its bevel angle.

FIG. 7 shows a graph of a levels of a direct beam D_B and an indirect beam I_B for a silica optical fiber with NA=0.28, and with bevel angle B_A. As seen, for small bevel angles B_A_1, i.e. sharp needles, a small change in bevel angle B_A results in a large change in ratio between direct and indirect light. Thus, this bevel angle range B_A_1, especially below some 23°, light output will depend highly on even small production tolerances. By using a bevel angle B_A of above 28°, almost all of the light in tissue will be in the direct beam, meaning that it is not influenced by the buffer or glue around the optical fiber. In addition, above 30°, the needle is robust for variation of the bevel angle B_A, meaning that manufacturing tolerances will not affect the light output in tissue. Combined with the silica core of the fiber and a glass-on-glass connector at a disposable product, this results in a disposable product where the optical characteristics are robust for manufacturing tolerances and for aging during the shelve life because only silica is involved in the optical path. Below 35° the fiber and needle has been found to be still sharp enough to allow easy insertion in relevant biological tissue, and still it will provide a low tissue sticking tendency. Thus, the inventive bevel angle range is 30°-35°, indicated by the dashed lines.

To summarize, the invention provides a medical needle which comprises an elongate tube and at least one optical fiber, e.g. two fibers, arranged within the elongate tube, for making optical measurements at the distal end of the needle. The optical fibers(s) has a beveled distal end surface, wherein a plane touching the beveled distal end surface and a longitudinal extension axis of the optical fiber forms a bevel angle which is 30°-35°. Such needle is advantageous for providing a medical needle which is reliable and long term stable, can be manufactured in low cost using known optical fiber materials, thus allowing it to form part of disposable medical kits. Still, the bevel angle of 30°-35° provides a needle which is easy to insert and which provides a low tendency to cause tissue sticking. Especially, the elongate tube and the optical fiber end(s) have the same beveled angle within the range 30°-35°, thus allowing a smooth front surface of the needle.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

The invention claimed is:

1. A needle comprising:
    an elongate tube (T) having a beveled distal end, and
    at least one optical fiber (FB1, FB2) arranged within the elongate tube (T), wherein the optical fiber (FB1, FB2) has a beveled distal end surface, wherein a plane touching the beveled distal end surface and a longitudinal extension axis of the optical fiber (FB1, FB2) forms a bevel angle (B_A) selected within a bevel angle range of 30.5°-34.5°.

2. Needle according to claim 1, wherein a plane touching the beveled distal end of the elongate tube (T) and a longitudinal extension axis of the elongate tube (T) forms an angle within said bevel angle range.

3. Needle according to claim 1, wherein a plane touching the beveled distal end of the elongate tube (T) and a longitudinal extension axis of the elongate tube (T) forms an angle which is equal to or substantially equal to said bevel angle (B_A).

4. Needle according to claim 1, wherein the plane touching the beveled distal end surface of the optical fiber (FB1, FB2) and the plane touching the beveled distal end of the elongate tube (T) are substantially parallel.

5. Needle according to claim 1, wherein the beveled distal end surface of the at least one optical fiber (FB1, FB2) is plane.

6. Needle according to claim 1, wherein the beveled distal end surface of the at least one optical fiber (FB1, FB2) is polished.

7. Needle according to claim 1, comprising a second optical fiber (FB2) arranged within the elongate tube (T), wherein a plane touching the beveled distal end surface of the second optical fiber (FB2) and a longitudinal extension axis of the second optical fiber (FB2) forms a bevel angle (B_A) selected within said bevel angle range.

8. Needle according to claim 7, wherein the plane touching the beveled distal end surface of the first optical fiber (FB1), the plane touching the beveled distal end surface of second optical fiber (FB2), and the plane touching the beveled distal end of the elongate tube (T) are all substantially parallel.

9. Needle according to claim 1, wherein said bevel angle range is one of: 30°-32°, 31°-33°, 32°-34°, and 33°-35°.

10. Needle according to claim 1, wherein said bevel angle range is one of: 31.0°-34.0°, 31.5°-33.5°, and 32.0°-33.0°.

11. Needle according to claim 1, wherein the optical fiber (FB1, FB2) is made of a material comprising silica.

12. Needle according to claim 11, wherein the optical fiber (FB1, FB2) is made of undoped fused silica.

13. Needle according to claim 11, wherein the optical fiber (FB1, FB2) is made of F-doped fused silica.

14. Needle according to claim 1, wherein the at least one optical fiber (FB1, FB2) is arranged within a stylet insert, wherein the stylet insert has a bevel at the distal end that has substantially the same bevel angle as the beveled distal end of the elongate tube (T), and the stylet insert is arranged within the elongate tube (T) such that a plane touching the beveled distal end of the elongate tube (T), and a plane touching the beveled distal end of the stylet insert are substantially parallel.

15. Interventional medical device comprising the needle of claim 1.

16. Method for optical probing in biological tissue, the method comprising:
    providing at least one optical fiber (FB1, FB2) with a beveled distal end surface, wherein a plane touching the beveled distal end surface and a longitudinal extension axis of the at least one optical fiber (FB1, FB2) forms a bevel angle (B_A) selected within a bevel angle range of 30.5°-34.5°, and
    applying light to or receiving light from the biological tissue through the beveled end surface of the at least one optical fiber (FB1 FB2).

* * * * *